United States Patent [19]
Hirota et al.

[11] Patent Number: 5,969,236
[45] Date of Patent: Oct. 19, 1999

[54] PARTICLE SENSOR

[75] Inventors: Toshikazu Hirota, Kuwana; Kazuyoshi Shibata, Nagoya, both of Japan

[73] Assignee: NGK Insulators, Ltd., Japan

[21] Appl. No.: 08/911,704

[22] Filed: Aug. 15, 1997

[30] Foreign Application Priority Data

Aug. 20, 1996 [JP] Japan .................................. 8-218816

[51] Int. Cl.$^6$ .............................. G01N 15/06; G01F 1/66; G01F 1/30; H01L 41/04
[52] U.S. Cl. .................. 73/61.75; 73/861.21; 73/861.73; 310/338
[58] Field of Search .............................. 73/61.75, 861.04, 73/861.21, 861.73, 61.79, 61.45, 61.49, 861.18; 310/311, 323, 324, 325, 328, 338, 358

[56] References Cited

U.S. PATENT DOCUMENTS

| | | | |
|---|---|---|---|
| 3,557,616 | 1/1971 | Landon, Jr. et al. ................ | 73/861.73 |
| 3,653,253 | 4/1972 | Olin ...................................... | 73/61.75 |
| 3,715,911 | 2/1973 | Chuan ................................... | 73/24.03 |
| 3,805,591 | 4/1974 | Willis et al. ........................... | 73/24.03 |
| 3,816,773 | 6/1974 | Baldwin et al. ....................... | 73/61.75 |
| 3,857,049 | 12/1974 | Zoltan .................................. | 310/328 |
| 4,212,190 | 7/1980 | Coover et al. . | |
| 4,240,287 | 12/1980 | Mast et al. ............................. | 73/61.75 |
| 4,432,228 | 2/1984 | Kruschmierz et al. ................ | 310/338 |
| 4,607,228 | 8/1986 | Reif ...................................... | 324/454 |
| 4,872,335 | 10/1989 | Tsuroka et al. ....................... | 73/24.01 |
| 5,098,657 | 3/1992 | Blackford et al. .................... | 422/73 |
| 5,201,322 | 4/1993 | Henry et al. .......................... | 73/861.21 |
| 5,257,530 | 11/1993 | Beattie et al. ......................... | 73/61.75 |
| 5,455,475 | 10/1995 | Josse et al. ............................ | 310/338 |
| 5,616,872 | 4/1997 | O'Brien ................................ | 73/61.75 |
| 5,698,931 | 12/1997 | Shibata et al. ........................ | 310/328 |
| 5,747,671 | 5/1998 | Hirota et al. .......................... | 73/61.75 |

FOREIGN PATENT DOCUMENTS

| | | |
|---|---|---|
| 0766086 | 9/1996 | European Pat. Off. . |
| 0769695 | 10/1996 | European Pat. Off. . |
| 2241783 | 3/1991 | United Kingdom . |
| 2294551 | 10/1994 | United Kingdom . |

Primary Examiner—Harshad Patel
Assistant Examiner—Robin Clark
Attorney, Agent, or Firm—Wall Marjama Bilinski & Burr

[57] ABSTRACT

A particle sensor includes, a sensor element including (a) a vibrating section having a mass that is sensitive to the collision of solid particles contained in a fluid with the vibrating section and (b) a detecting section for detecting the vibration of the vibrating section caused by the collision and converting the vibration to electric signals, a housing for fixing said sensor element, an inlet nozzle forming a fluid inlet, and an outlet nozzle forming a fluid outlet. In the particle sensor, the outlet nozzle is provided so that the sensor element is between the inlet nozzle and the outlet nozzle, throughholes are formed in the sensor element in at least part of the vicinity of the vibrating section, and the fluid entering the particle sensor from the inlet nozzle collides with the sensor element, passes through the throughholes and leaves the particle sensor from the outlet nozzle. The particle sensor has such a characteristic structure that the speed of a fluid colliding with the sensor element can be changed. The particle sensor can measure the sizes and particle size distribution of particles contained in a fluid, easily in a short time.

9 Claims, 6 Drawing Sheets

PARTICLE SENSOR

BACKGROUND OF THE INVENTION

1. Field of the Invention

The present invention relates to a particle sensor for detecting the solid particles contained in a fluid.

2. Description of Related Art

When solid particles are present in a fluid (a liquid or a gas), it is necessary in some cases to detect the presence of the particles. Detection of such particles is particularly important when the particles present in the fluid badly affect the intended action of the fluid.

Lubricating oils (e.g. engine oils) are used in internal combustion engines of automobiles or heavy machinery in order to reduce the frictional resistance and abrasion of the rotating surfaces and sliding surfaces of the engines. Operation of such internal combustion engines generates particles (e.g. metal fine particles) caused by abrasion. The particles are taken into the lubricating oils and may accelerate the abrasion of the rotating surfaces and sliding surfaces. The particles present in the lubricating oils are ordinarily removed by the use of a filter such as oil filter or the like. The condition of the lubricating oils can be monitored in detail by detecting the particles present in the lubricating oils.

Hydraulic oils and flushing oils are used in power transmission mechanisms (e.g. transmission), oil hydraulic pipe systems (e.g. oil hydraulic servo valve), rolling, pressing, etc. It is important to control the condition of these oils by detecting the solid particles present in the oils and/or examining the viscosities of the oils.

It is also important to detect the particles suspended in the air or examine their concentration in the air in order to monitor the level of air pollution. Such detection includes detection of the particles suspended in the exhaust gas discharged from a plant, a factory or the like.

As a sensor for detecting particles contained in a fluid, there is disclosed a particle sensor comprising a sensor element using a piezoelectric film, in Japanese Patent Application Laid-Open (Kokai) No. 7-301594. With this sensor, particles present in a fluid collide with the detecting section (having a piezoelectric film) of the sensor element or with the vibrating section (mounting the detecting section thereon) of the sensor element. As a result the vibrating section and the detecting section are vibrated, and the piezoelectric film converts the vibration into electric signals. These electric signals are outputted by electrodes holding the piezoelectric film between them.

In order to maintain the condition of a fluid at an intended level by, for example, conducting filtration as necessary, it is useful to know information not only on the presence or concentration of particles in the fluid but also on the sizes or particle size distribution of these particles. In detecting particles present in a fluid using the above-mentioned conventional particle sensor, the speed of the fluid hitting the sensor element of the sensor is set at a given constant level and, in this state, the amplitude (voltage) of each signal generated by the collision of particles in the fluid, with the sensor element is measured to determine the particle sizes.

The measured values of amplitude of each signal, however, show high scattering and have low accuracy. Increase in times of measurement for higher accuracy in turn increases the complexity of signal processing, and also requires a longer time for measurement.

SUMMARY OF THE INVENTION

The present invention is intended to overcome these limitations. The present invention is intended to provide a particle sensor which can measure the sizes and particle size distribution of particles present in a fluid, easily in a short time.

According to the first aspect of the present invention, there is provided a particle sensor comprising:

a sensor element comprising (a) a vibrating section having such a mass that is sensitive-to the collision of solid particles contained in a fluid, with the vibrating section and (b) a detecting section for detecting the vibration of the vibrating section caused by said collision and converting the vibration to electric signals, a housing for fixing said sensor element, an inlet nozzle forming a fluid inlet, and an outlet nozzle forming a fluid outlet, in which particle sensor said outlet nozzle is provided so that the sensor element is between the inlet nozzle and the outlet nozzle, throughholes are formed in the sensor element in at least part of the vicinity of the vibrating section, and the fluid entering the particle sensor from the inlet nozzle collides with the sensor element, passes through the throughholes and leaves the particle sensor from the outlet nozzle, which particle sensor has such a characteristic structure that the speed of a fluid colliding with the sensor element can be changed.

According to the second aspect of the present invention, there is provided a particle sensor constituted by combining a plurality of sensors each comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, an inlet nozzle forming a fluid inlet, and an outlet nozzle forming a fluid outlet, in each of which sensors said outlet nozzle is provided so that the sensor element is between the inlet nozzle and the outlet nozzle, throughholes are formed in the sensor element in at least part of the vicinity of the vibrating section, and the fluid entering the particle sensor from the inlet nozzle collides with the sensor element, passes through the throughholes and leaves the particle sensor from the outlet nozzle, which particle sensor has such a characteristic structure that a fluid is allowed to collide with the sensor elements of the individual sensors at different speeds.

In the present invention, "speed" of fluid refers to a volume of a fluid which passes the unit area of the cross-section of the flow path of the fluid in a unit time, and is expressed by a unit of, for example, $m^3/m^2 \cdot sec$ (=m/sec).

BRIEF DESCRIPTION OF DRAWINGS

FIGS. 3(a) and 3(b) each show the sensor element used in the basic structure of FIG. 1.

DETAILED DESCRIPTION OF THE PREFERRED EMBODIMENTS

Figure 1:
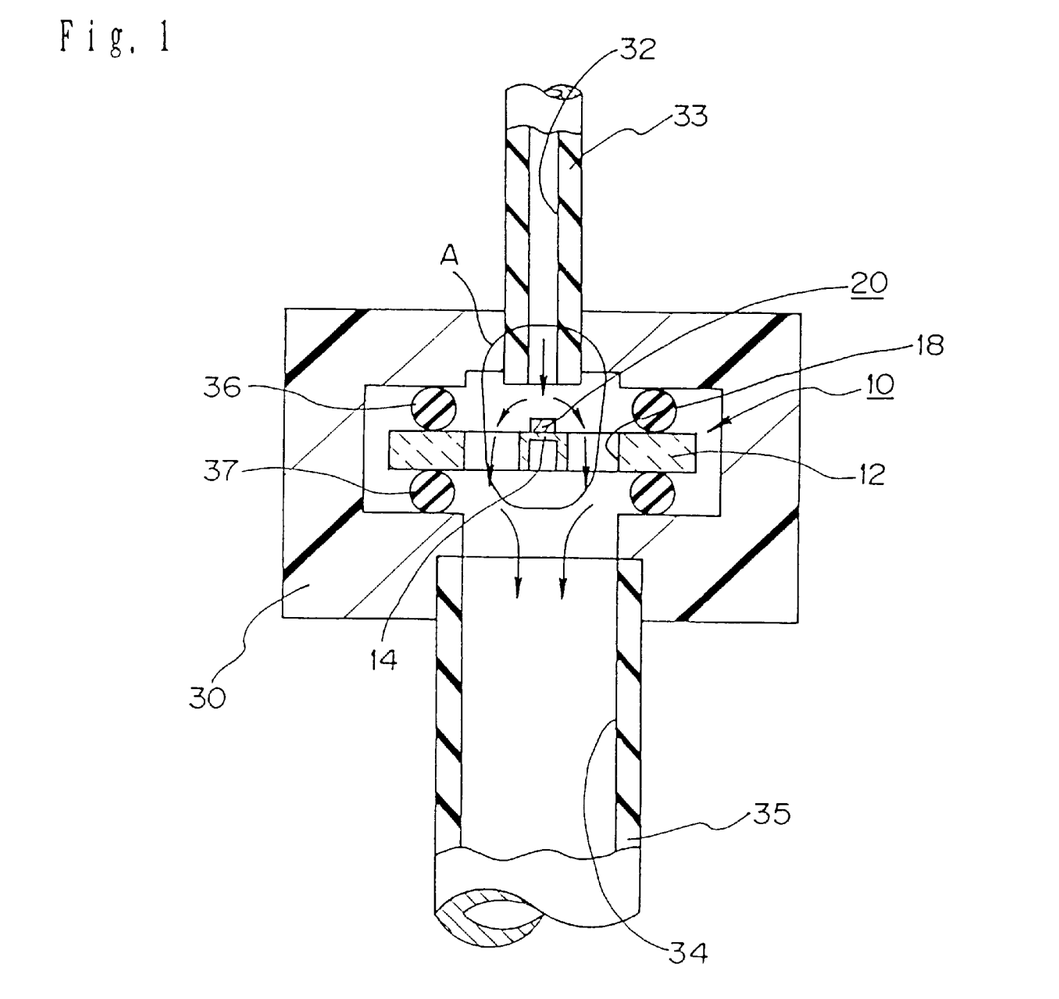
FIG. 1 is a sectional view of an example of the basic structure of the particle sensor according to the present invention.
Figure 2:
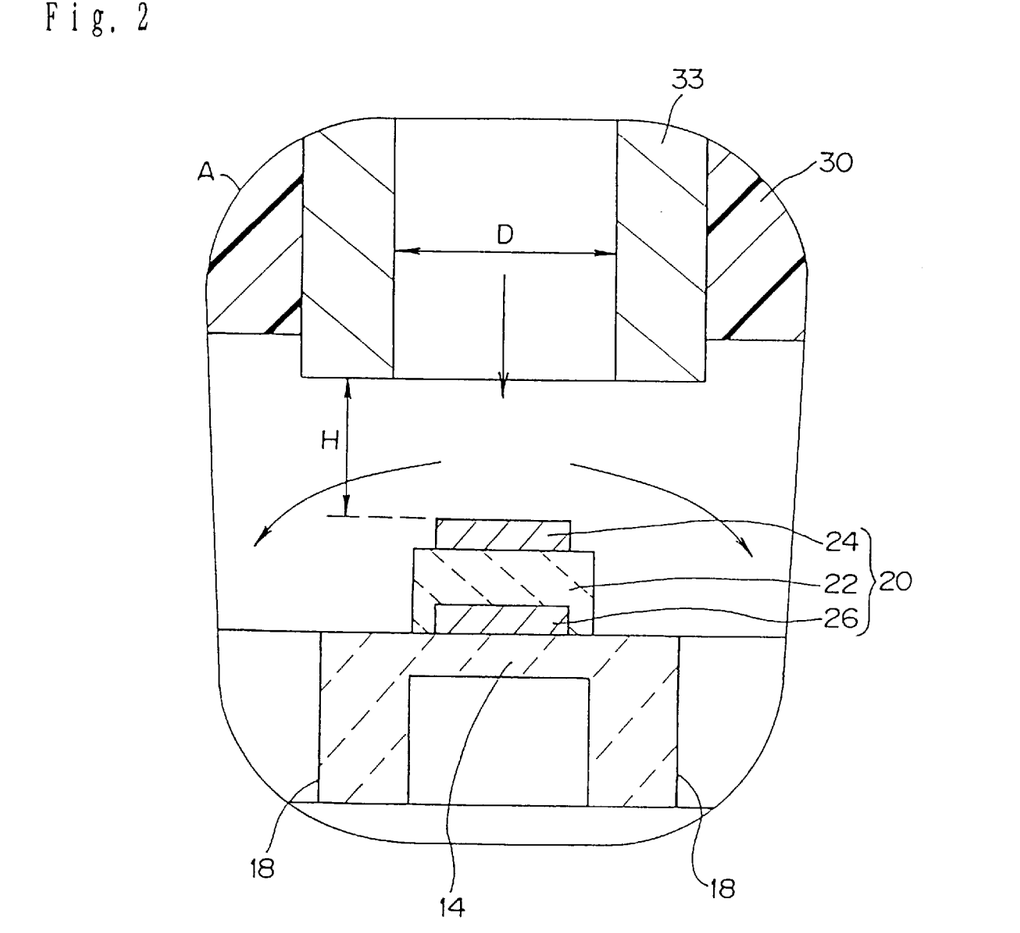
FIG. 2 is an enlarged view of the portion A of FIG. 1.

First, description is made on the particle sensor according to the first aspect of the present invention. FIG. 1 is a sectional view showing an example of the basic structure of the particle sensor according to the present invention, and FIG. 2 is an enlarged view of the portion A of FIG. 1. In this sensor, the flow path of a fluid is constituted by an inlet nozzle 33 forming the inlet 32 of the fluid, an outlet nozzle 35 forming the outlet 34 of the fluid, and a housing 30 to which the nozzles 33 and 35 are fixed and which accommodates a sensor element 10 between the inlet nozzle 33 and the outlet nozzle 35.

The outlet nozzle 35 is provided so that the sensor element 10 is located between the inlet nozzle 33 and the outlet nozzle 35. At least part of the portion of the sensor element 10 in the vicinity of the vibrating section 14 has throughholes 18. The vibrating section 14 of the sensor element 10 is provided in the flow direction of the fluid determined by the inlet nozzle 33 so that the fluid from the inlet nozzle 33 can collide with the sensor element 10, pass through the throughholes 18, and leave the sensor from the outlet nozzle 35. The sensor element 10 is fixed to the inside of the housing 30 via elastic members 36 and 37 (e.g. O-rings).

FIGS. 3(a) and 3(b) show an example of the sensor element 10 used in the basic structure of particle sensor of FIG. 1. FIG. 3(a) is a plan view of the sensor element 10 and FIG. 3(b) is a sectional view of the sensor element 10 taken at the I—I line of FIG. 3(a). The vibrating section 14 is a thin plate and is fixed to a fixing section 16 so that the vibrating section 14 can. The vibrating section 14 and the fixing section 16 forms a one-piece body 12. A hollow 17 is formed in the body 12 so that the vibrating section 14 can become a thin plate. On one surface 14 s of the vibrating section 14 opposite to its surface facing the hollow 17 is provided a detecting section 20. In the portion of the body 12 in the vicinity of the vibrating section 14 are formed a pair of throughholes 18 penetrating the body 12 in the thickness direction.

In FIG. 1, a fluid enters the housing 30 through the inlet nozzle 33 and contacts with the vibrating section 14 and the detecting section 20 mounted on the vibrating section 14, in such a way that the fluid flow is interrupted by the contact as shown by the arrows. At this time, the particles present in the fluid collide with the vibrating section 14 and the detecting section 20. This causes the vibrating section 14 and the detecting section 20 to vibrate. After contact with the vibrating section 14 and the detecting section 20, the fluid passes through the throughholes 18 and the outlet nozzle 35, and leaves the sensor. With this sensor, particles present in a fluid collide with the detecting section 20 (having a piezoelectric film) of the sensor element 10 or with the vibrating section 14 (mounting the detecting section 20 thereon) of the sensor element. As a result the vibrating section 14 and the detecting section 20 are vibrated causing the piezoelectric film 22 to convert the vibration into electric signals. These electric signals are outputted by electrodes 24, 26 holding the piezoelectric film between them.

The particle sensor according to the first aspect of the present invention has the above-mentioned basic structure and further has such a characteristic structure that the speed of a fluid colliding with the sensor element 10 can be changed. In this sensor, when a fluid collides with the sensor element at a larger speed, the particles contained in the fluid give larger impacts to the sensor element 10. Consequently, even smaller particles can be detected. Therefore, by changing the speed of a fluid colliding with the sensor element 10, the minimum diameter of the particles detectable by the sensor differs.

By using such a sensor in which the speed of a fluid colliding with the sensor element 10 can be changed and by allowing a fluid to collide with the sensor element 10 at various different speeds, there can be known, at each speed employed, the presence of particles of minimum detectable diameter and larger particles. By determining, in advance, the minimum detectable particle diameters at various speeds, the sizes of the particles contained in a fluid can be known quickly by simply examining the generation of signals by the sensor at various speeds. Further, by examining the number of the particles detected at each speed in a given length of time, there can be known the particle size distribution of the particles contained in the fluid.

Next, with respect to the particle sensor according to the first aspect of the present invention, description is made on examples of the specific means for changing the speed of a fluid colliding with the sensor element 10, and also on examples of the constitution of the particle sensor using such a means.

Figure 4:
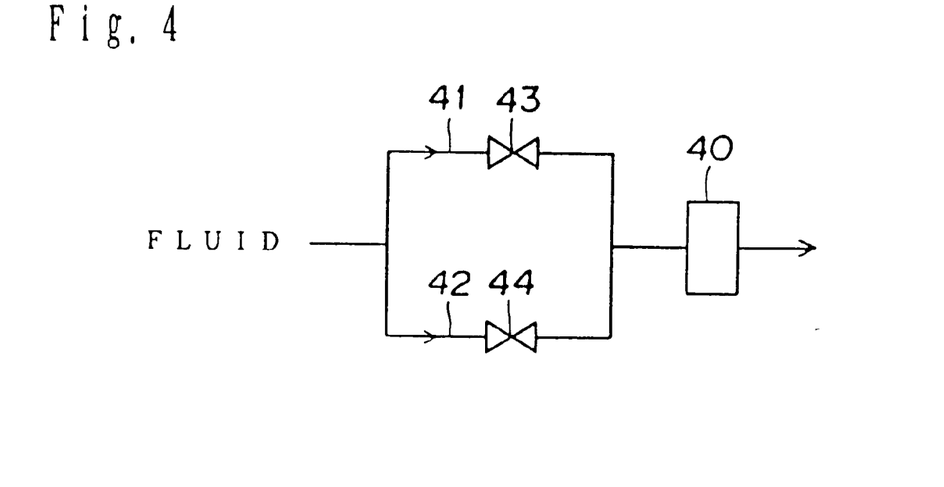
FIG. 4 is a schematic drawing showing an example of the constitution of the particle sensor according to the first aspect of the present invention.

The first means for changing the speed of a fluid colliding with the sensor element 10 of particle sensor comprises dividing a portion of fluid flow path located upstream of the inlet nozzle 33 of particle sensor 40, into a plurality of branch flow paths; allowing each branch flow path to have a switching valve 43 and 44; and changing the opening state of each valve 43 and 44. FIG. 4 shows an example of the particle sensor 40 constituted by using such a means. In this example, a portion of fluid flow path located upstream of the inlet nozzle 33 of a particle sensor 40 is divided into two branch flow paths 41 and 42. Moreover switching valves 43 and 44 are provided in the branch flow paths 41 and 42, respectively. By changing the opening states of the switching valves 43 and 44, the speed of a fluid colliding with the sensor element 10 of the particle sensor 40 can be changed.

In the example of FIG. 4, when the branch flow path 41 and the branch flow path 42 have the same inner diameter, two different fluid speeds can be obtained by (1) opening either of the valves 43 and 44 and (2) opening both of the valves 43 and 44. When the branch flow path 41 and the second branch flow path 42 have different inner diameters, three different fluid speeds can be obtained by (1) opening only the valve 43, (2) opening only the valve 44 and (3) opening both of the valves 43 and 44.

Figure 5:
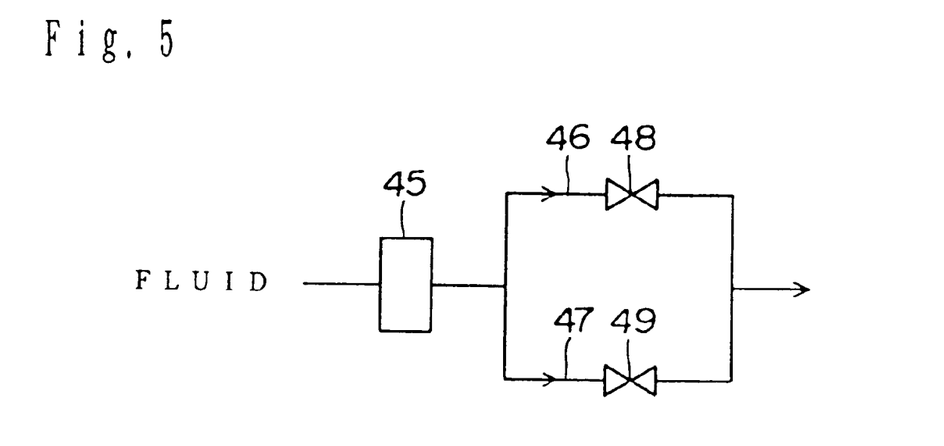
FIG. 5 is a schematic drawing showing an example of the constitution of the particle sensor according to the first aspect of the present invention.

The second means for changing the speed of a fluid colliding with the sensor element 10 of particle sensor comprises dividing a portion of fluid flow path located downstream of the outlet nozzle 35 of particle sensor 45, into a plurality of branch flow paths, allowing each branch flow path to have a switching valve 48 and 49, and changing the opening state of each valve 48 and 49. FIG. 5 shows an example of the particle sensor constituted by using such a means. In this example, a portion of fluid flow path located downstream of the outlet nozzle 35 of a particle sensor 45 is divided into two branch flow paths 46 and 47. Switching valves 48 and 49 are provided in the branch flow paths 46 and 47, respectively. By changing the opening states of the switching valves 48 and 49, the speed of a fluid colliding with the sensor element 10 of the particle sensor 45 can be changed.

Figure 6:
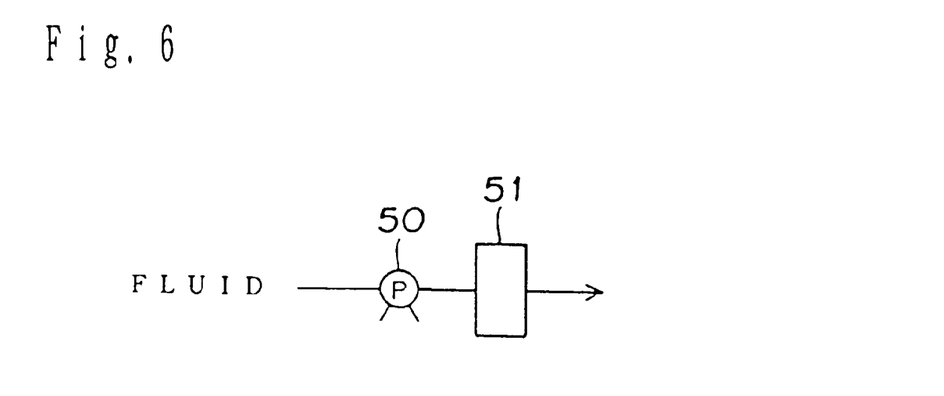
FIG. 6 is a schematic drawing showing an example of the constitution of the particle sensor according to the first aspect of the present invention.

The other means for changing the speed of a fluid colliding with the sensor element 10 of particle sensor comprises, for example as shown in FIG. 6, providing a pump 50 at a flow path portion located upstream of the inlet nozzle 33 of a particle sensor 51 and changing the discharge amount of the pump 50 to change the speed of a fluid colliding with the sensor element 10 of the particle sensor 51. Alternatively, the speed of a fluid colliding with the sensor element 10 of particle sensor may be changed by as necessary changing the diameter of the inlet 33 or outlet 35 nozzle of particle sensor 40, or by as necessary changing the distance between inlet nozzle 35 top end and sensor element 10. In the first aspect of the present invention, the examples of the specific means for changing the speed of a fluid colliding with the sensor element 10 and also the examples of the constitution of the particle sensor 40 using such a means are not restricted to those mentioned above.

Figure 3:
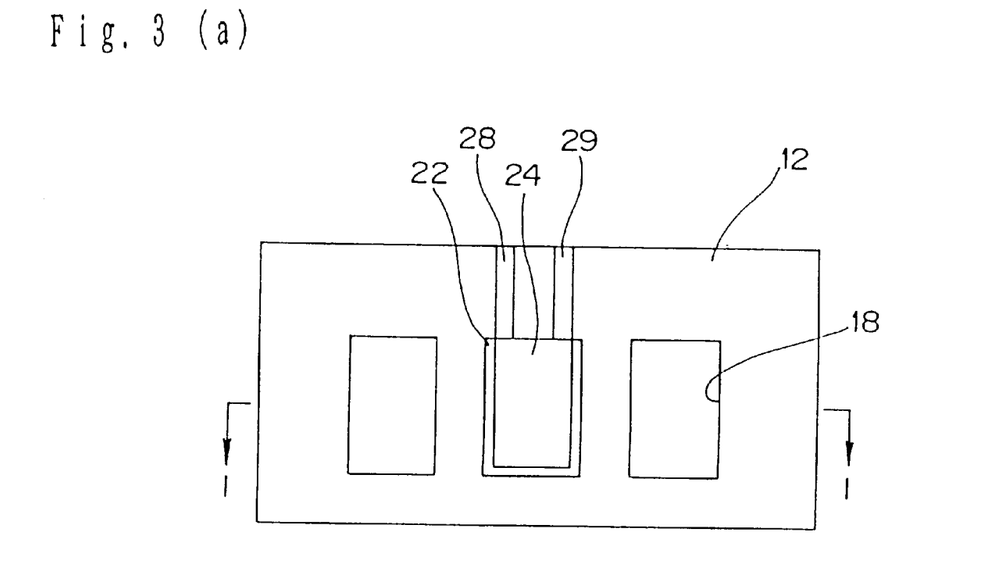
FIG. 3(a) is a plan view of the sensor element and FIG. 3(b) is a sectional view of the sensor element taken at the I—I line of FIG. 3(a).

Then, description is made on the particle sensor 40 according to the second aspect of the present invention. The particle sensor according to the second aspect of the present invention comprises a plurality of sensors each having the above-mentioned basic structure as shown in FIGS. 1–3. This also allows fluid to collide with the sensor elements of the individual sensors at different speeds. In this sensor, when a fluid collides with each sensor element 10 at a larger speed, the particles contained in the fluid give larger impacts to each sensor element 10. As a result, even smaller particles can be detected. Therefore, by changing the speed of a fluid colliding with each sensor element 10, the minimum diameter of the particles detectable by each sensor differs.

By passing a fluid through a plurality of sensors each different in minimum detectable particle diameter, there can be known, by each sensor, the presence of particles of minimum detectable diameter and larger particles. By determining, for each sensor, the minimum detectable particle diameter beforehand, the sizes of the particles contained in a fluid can be known quickly by simply examining the generation of signals by each sensor. Further, by examining the number of the particles detected in each sensor in a given length of time, there can be known the particle size distribution of the particles contained in the fluid.

Next, with respect to the particle sensor according to the second aspect of the present invention, description is given of examples of the specific means for allowing a fluid to collide with the sensor elements of the individual sensors at different speeds. Descriptions are also provided of examples of the constitution of the particle sensor using such a means.

Figure 7:
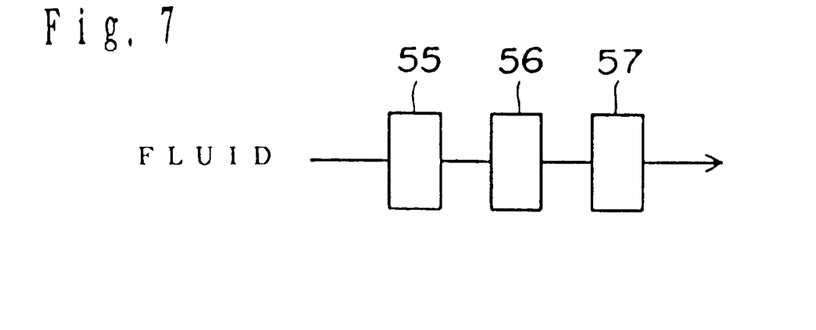
FIG. 7 is a schematic drawing showing an example of the constitution of the particle sensor according to the second aspect of the present invention.

As indicated by FIG. 7, the first means for allowing a fluid to collide with the sensor elements of the individual sensors at different speeds comprises allowing the inlet nozzles of the individual sensors to have different inner dimameters. When the amount of fluid fed into sensor element 10 is constant, a smaller inner diameter of inlet nozzle 33 gives a fluid of higher speed. FIG. 7 shows an example of the particle sensor 40 constituted by using such a means. This particle sensor 40 is constituted by combining, in series, a first sensor 55, a second sensor 56 and a third sensor 57, each having a different inner diameter D of inlet nozzle 33, as shown in FIG. 2.

In each of the first to third sensors 55–57, the distance H between the top end of inlet nozzle 33 and sensor element was set at 0.1 mm. The inner diameter D of inlet nozzle 33, the fluid speed at inlet nozzle 33 top end, and the minimum detectable particle diameter (when the particles contained in fluid was $Al_2O_3$ particles), in each sensor were as shown in Table 1.

In this particle sensor, $Al_2O_3$ particles having particle diameters of 25 μm or more can be detected by any of the first sensor 55, the second sensor 56 and the third sensor 57. On the other hand, $Al_2O_3$ particles having particle diameters of 10 μm to less than 25 μm can be detected by the second sensor 56 and the third sensor 57. By contrast, $Al_2O_3$ particles having particle diameters of 5 μm to less than 10 μm can be detected only by the third sensor 57. Thus by examining, in each of the first to third sensors 55–57, the number of particles detected in a given length of time, there can be known the particle size distribution of particles contained in a fluid.

TABLE 1

|  | Inner diameter of inlet nozzle (mm) | Fluid speed at top end of inlet nozzle (m/sec) | Minimum detectable particle diameter (μm) |
| --- | --- | --- | --- |
| First sensor | 3.5 | 3.7 | 25 |
| Second sensor | 3 | 5 | 10 |
| Third sensor | 2.5 | 7.2 | 5 |

Figure 8:
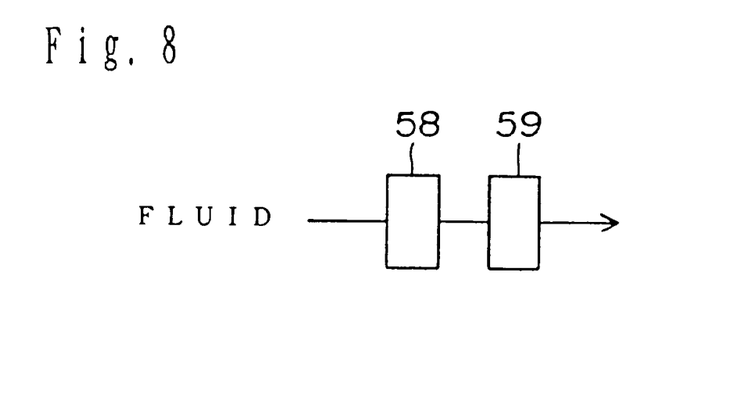
FIG. 8 is a schematic drawing showing an example of the constitution of the particle sensor according to the second aspect of the present invention.

As indicated by FIG. 8, the second means for allowing a fluid to collide with the sensor elements 10 of the individual sensors at different speeds comprises allowing the distances between inlet nozzle 33 top end and sensor element 10, of the individual sensors to have different values. FIG. 8 shows an example of such a particle sensor constituted. This particle sensor is constituted by combining, in series, a first sensor 58 and a second sensor 59, each having a different distance H between the top end of inlet nozzle 33 and sensor element 10, shown in FIG. 2.

In each of the first sensor 58 and the second sensor 59, the inner diameter D of inlet nozzle 33 was set at 3 mm and the fluid speed at the top end of inlet nozzle 33 was set at 5 m/sec. For each sensor, the distance H between the top end of inlet nozzle 33 and sensor element 10, along with the minimum detectable particle diameter (when the particles contained in fluid were $Al_2O_3$ particles) are shown in Table 2.

TABLE 2

|  | Distance between inlet nozzle top end and sensor element (mm) | Minimum detectable particle diameter ($\mu$m) |
| --- | --- | --- |
| First sensor | 0.1 | 10 |
| Second sensor | 1 | 40 |

Figure 9:
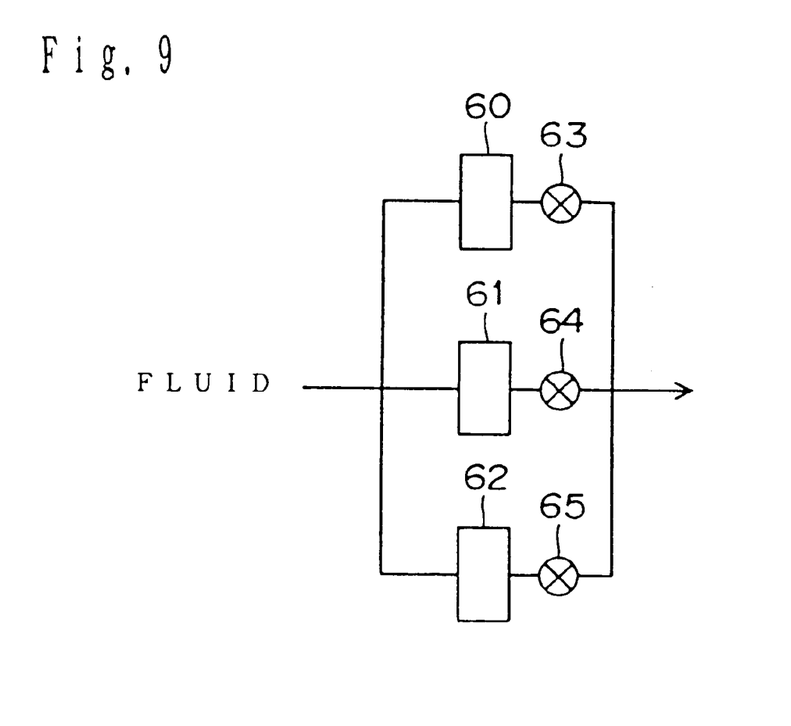
FIG. 9 is a schematic drawing showing an example of the constitution of the particle sensor according to the second aspect of the present invention.

As indicated by FIG. 9, the third means for allowing a fluid to collide with the sensor elements 10 of the individual sensors at different speeds allows a fluid to have different flow resistances downstream of the individual sensors. The control of the flow resistance of fluid downstream of each sensor 60–62 can be made, for example, by providing a valve 63–65 downstream of the outlet nozzle 35 of each sensor 60–62 and changing the opening degree of each valve 63–65. FIG. 9 shows an example of such a particle sensor. This particle sensor is constituted by combining a first sensor 60, a second sensor 61 and a third sensor 62 in parallel and providing valves 63, 64 and 65 downstream of the respective outlet nozzles. In this particle sensor, by changing the opening degrees of the valves 63–65, the flow resistances of fluid downstream of the sensors 60–62 are made different.

In each of the first to third sensors 60–62, the inner diameter D of inlet nozzle 33 was set at 3 mm and the distance H between inlet nozzle 33 top end and sensor element 10 was set at 0.2 mm. In each sensor, the fluid speed at inlet nozzle top end, and the minimum detectable particle diameter (when the particles contained in fluid were $Al_2O_3$ particles) are shown in Table 3.

TABLE 3

|  | Fluid speed at top end of inlet nozzle (m/sec) | Minimum detectable particle diameter ($\mu$m) |
| --- | --- | --- |
| First sensor | 3 | 30 |
| Second sensor | 5 | 15 |
| Third sensor | 7 | 10 |

Figure 10:
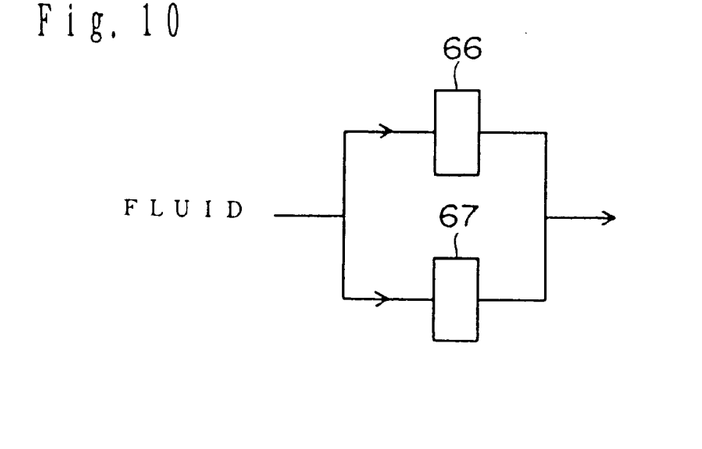
FIG. 10 is a schematic drawing showing an example of the constitution of the particle sensor according to the second aspect of the present invention.

As indicated by FIG. 10, the fourth means for allowing a fluid to collide with the sensor elements of the individual sensors at different speeds comprises allowing a fluid to have different flow resistances upstream of the sensor elements of the individual sensors. The control of the flow resistance of fluid upstream of each sensor element 10 can be made, for example, by changing the shape or inner wall surface roughness of the inlet nozzle 10 of each sensor. FIG. 10 shows an example of such a particle sensor. In this particle sensor, a first sensor 66 and a second sensor 67 are combined in parallel and the flow resistance of fluid upstream of the sensor element 10 of each sensor 66–67 is made different.

In each of the first sensor 66 and the second sensor 67, the inner diameter D of inlet nozzle 10 was set at 2 mm, while the distance H between inlet nozzle 10 top end and sensor element 10 was set at 1 mm. In each sensor, the fluid speed at inlet nozzle 33 top end and the minimum detectable particle diameter (when the particles contained in fluid were $Al_2O_3$ particles) were as shown in Table 4.

TABLE 4

|  | Fluid speed at top end of inlet nozzle (m/sec) | Minimum detectable particle diameter ($\mu$m) |
| --- | --- | --- |
| First sensor | 5 | 50 |
| Second sensor | 20 | 10 |

Figure 11:
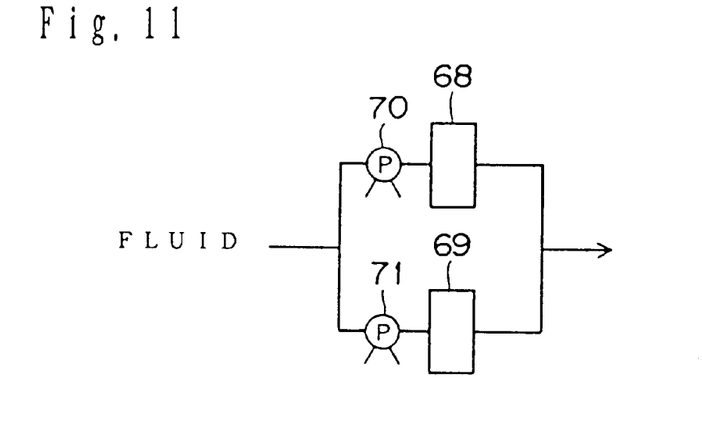
FIG. 11 is a schematic drawing showing an example of the constitution of the particle sensor according to the second aspect of the present invention.

As indicated by FIG. 11, the fifth means for allowing a fluid to collide with the sensor elements of the individual sensors at different speeds comprises allowing a fluid to be fed into the sensor elements 10 of the individual sensors 68–69 at different amounts per unit time. The control of the amount of fluid fed into each sensor element 68–69 can be made, for example, by providing a pump 70–71 upstream of each inlet nozzle 33 of each sensor. FIG. 11 shows an example of such a particle sensor. In this particle sensor, a first sensor 68 and a second sensor 69 are combined in parallel, while a pump 70 and a pump 71 are provided upstream of the respective inlet nozzles. By the action of these pumps, a fluid is fed into the first sensor and the second sensor at different amounts per unit time.

In each of the first sensor 68 and the second sensor 69, the inner diameter D of inlet nozzle 33 was set at 1 mm and the distance H between inlet nozzle 33 top end and sensor element 10 was set at 0.5 mm. In each sensor, the fluid speed at inlet nozzle 10 top end, and the minimum detectable particle diameter (when the particles contained in fluid were $Al_2O_3$ particles) are shown in Table 5.

TABLE 5

|  | Fluid speed at top end of inlet nozzle (m/sec) | Minimum detectable particle diameter ($\mu$m) |
| --- | --- | --- |
| First sensor | 5 | 20 |
| Second sensor | 30 | 5 |

Of the above first to fifth means, the first to third means are simple and can effectively allow a fluid to collide with a plurality of sensor elements at different speeds. In the third to fifth means, the individual sensors can have the same sensor structure (arrangements and dimensions of various sensor parts) in the vicinity of the surface of sensor element 10 with which a fluid collides.

The first to fifth means can be employed in any combination. For example, in the particle sensor of FIG. 12, there are combined different inner diameters of inlet nozzle, different distances between inlet nozzle top end and sensor element 10 and different flow resistances of fluid downstream of sensor, whereby a fluid can collide with the sensor elements of the first sensor 72, the second sensor 73, the third sensor 74, the fourth sensor 75 and the fifth sensor 76 at different speeds. The fourth sensor 75 and the fifth sensor 76 are provided, downstream thereof, with valves 77 and 78, respectively, whereby the flow resistances of fluid downstream of the respective sensors are controlled. The details of the first to fifth sensors are shown in Table 6.

TABLE 6

Figure 12:
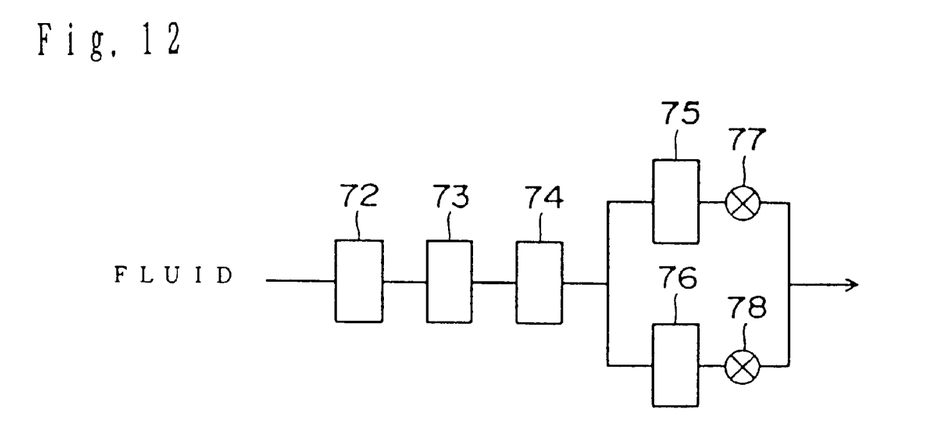
FIG. 12 is a schematic drawing showing an example of the constitution of the particle sensor according to the second aspect of the present invention.

|  | Inner diameter of inlet nozzle (mmφ) | Fluid speed at inlet nozzle top end (m/sec) | Distance between inlet nozzle top end and sensor element (mm) | Minimum detectable particle diameter (μm) |
| --- | --- | --- | --- | --- |
| First sensor | 2 | 7 | 0.1 | 5 |
| Second sensor | 2 | 7 | 0.2 | 10 |
| Third sensor | 3 | 3 | 0.3 | 20 |
| Fourth sensor | 2 | 5 | 0.2 | 15 |
| Fifth sensor | 2 | 2 | 0.2 | 50 |

According to the second aspect of the present invention, the means for allowing a fluid to collide with the sensor elements of individual sensors at different speeds and the constitution of the particle sensor are not restricted to those mentioned above. The number of sensors constituting the particle sensor, the speed of fluid colliding with the sensor element 10 of each sensor, the difference in minimum detectable particle diameter between sensors, etc. can be determined appropriately depending upon the kind of fluid or particles contained therein, the purpose of measurement, etc. In examining the sizes of particles by using the particle sensor of the present invention, it is possible to use, in combination, a conventional technique of examining the sizes of particles by the amplitudes of signals obtained, whereby particle diameters can be examined more exactly.

Next, description is made in detail on the constitution of each section of the sensor element 10 used in the particle sensor of the present invention. As indicated by DIGS. 2 and 3(b), the body 12 of the sensor element 10 has a hollow 17 in order to make thin the vibrating section 14, and through-holes 18 are formed around the vibrating section 14.

The vibrating section 14 need not be fixed to the fixing section 16 at the whole periphery as shown in FIG. 3(b), and may be fixed partially. For example, only one end of the whole periphery of the vibrating section 14 may be fixed to the fixing section 16. The hollow 17 is not restricted to such a hollow as shown in FIG. 3(b) and may be a closed space. The hollow 17 may be formed at the outlet 34 side, or may be formed at the inlet 32 side. The detecting section 20 may be provided at the inlet 32 side relative to the vibrating section 14, or may be provided at the outlet 34 side relative to the vibrating section 14.

There is no particular restriction as to the number, shape, etc. of the throughholes 18. However, it is preferable that one pair of the throughholes 18 have the same shape and are provided symmetrically with respect to a virtual plane penetrating the vibrating section 14 in the axial direction. The shape of the body 12 is preferably a plate, but has no particular restriction and can be appropriately determined depending upon the intended application of particles sensor.

The vibrating section 14, when collided by particles, vibrates, together with the detecting section 20, in a vertical direction, i.e. a direction extending to the detecting section 20 and the hollow 17. In order to detect this vibration, the vibrating section 14 is preferably a plate. The thickness of the vibrating section 14 is preferably 1–100 μm. When the thickness is more than 100 μm, the vibrating section 14 has a low sensitivity to collision; when the thickness is less than 1 μm, the vibrating section 14 has low mechanical strengths.

The vibrating section 14 is preferably composed of materials which are chemically stable and which undergo no chemical change in contact with various fluids containing solid particles to be detected. The vibrating section 14 is preferably made of a ceramic such as stabilized zirconia, partially stabilized zirconia, magnesia, mullite, aluminum nitride, silicon nitride, glass or the like. The fixing section 16 may be made of the same materials as used in the vibrating section 14, or of different materials.

The detecting section 20 has a piezoelectric film 22, a first electrode 24 and a second electrode 26 with the piezoelectric film 22 being sandwiched between the two electrodes. The first electrode 24 covers at least part of the surface 22s of the piezoelectric film 22, and the second electrode 26 covers at least part of the surface 14 s of the vibrating section 14. The piezoelectric film 22 causes, microscopically, dielectric polarization when a stress is applied thereto, and generates, macroscopically, an electric signal (e.g. electric charge or voltage) depending upon the level of the stress. At this time, it is preferable that the piezoelectric film 22 undergoes bending displacement in the thickness direction.

The piezoelectric film 22, when the particles present in a fluid contact with the first electrode 24 and/or the vibrating section 14, vibrates in its thickness direction together with the vibrating section 14. This vibration applies stress to the piezoelectric film 22, whereby the piezoelectric film 22 generates electric signals. The electric signals are output to terminal pads by the first electrode 24 and the second electrode 26 via leads 28 and 29.

The piezoelectric film 22 has a thickness of preferably 1–100 μm. When the thickness is more than 100 μm, the film has a low sensitivity, whereas when the thickness is less than 1 μm, the film is unreliable.

Preferably, the piezoelectric film is made of a piezoelectric ceramic. It may also be made of an electro-strictive ceramic or a ferroelectric ceramic. It may also be made of a material which needs a polarization treatment or no polarization treatment.

The ceramic used in the piezoelectric film includes, for example, a ceramic containing lead zirconate, magnesium lead niobate, nickel lead niobate, zinc lead niobate, manganese lead niobate, antimony lead stannate, lead titanate, manganese lead tungstate, cobalt lead niobate, barium titanate, or any combination-thereof. For example, a ceramic composed of magnesium lead niobate, lead zirconate and lead titanate at a ratio close to 20:37:43 has a high Curie point, superior piezoelectricity characteristics, and is suitable as a material for piezoelectric film.

The above ceramic may further contain an appropriate amount of an oxide of lanthanum, calcium, strontium, molybdenum, tungsten, barium, niobium, zinc, nickel, manganese or the like; any combination of said oxides; or other compound. For example, a ceramic composed mainly of magnesium lead niobate, lead zirconate and lead titanate and further containing lanthanum or strontium is preferred.

The first electrode 24 and the second electrode 26 can have appropriate thicknesses depending upon the application of the present particle sensor, but each thicknesses is preferably 0.1–50 μm.

The first electrode 24 is preferably composed of an electroconductive metal which is a solid at room temperature. The metal includes, for example, single metals such as aluminum, titanium, chromium, iron, cobalt, nickel, copper, zinc, niobium, molybdenum, ruthenium, rhodium, silver, tin, tantalum, tungsten, iridium, platinum, gold, lead and the like; and their alloys.

The second electrode 26 is preferably composed of a high-melting metal such as platinum, ruthenium, rhodium, palladium, iridium, titanium, chromium, molybdenum, tantalum, tungsten, nickel, cobalt or the like; or any alloy thereof. It is because the second electrode 26 may be exposed to high temperatures when the piezoelectric film 22 is subjected to a heat treatment and therefore the second electrode is preferably made of a metal resistive to a high-temperature oxidizing atmosphere. The second electrode 26 may be made of a cermet composed of the above-mentioned high-melting metal and a ceramic such as alumina, zirconium oxide, silicon oxide, glass or the like.

Next, description is made on the process for producing the sensor element 10 of the present particle sensor 40.

The body of the sensor element 10 is made in one piece by laminating a plurality of laminating layers (which are green sheets or green tapes) by hot pressing or the like and then sintering the laminate. For example, in the body 12 of FIG. 3(b) having a hollow 17, two laminating layers of green sheets or green tapes are laminated. Before the lamination, a throughhole of desired shape to become the hollow 17 is formed in the second layer. Alternatively, the layers may be formed by pressure molding, casting, injection molding or the like and the hollow may be formed by cutting, machining, laser processing, punching by pressing or the like. Although the laminating layers need not have the same thickness, it is preferred that the layers undergo similar shrinkages in sintering.

Formation of a detecting section 20 on the ceramic vibrating section 14 can be conducted as follows. A piezoelectric is formed by pressing using a mold or by tape forming using a material slurry. This piezoelectric before sintering is laminated on the vibrating section of the body before sintering by hot pressing, and sintering is conducted to form a body and a piezoelectric. In this case, electrodes must be formed on the body or the piezoelectric beforehand by a film forming method described later.

Although the sintering temperature for the piezoelectric film 22 is determined appropriately depending upon the materials of the film, the sintering temperature is generally 800–1,400° C., preferably 1,000–1,400° C. In this case, it is preferred for controlling the composition of the piezoelectric film 22 to conduct sintering in the presence of the evaporation source of the components of the piezoelectric film 22.

In the film forming method, a second electrode 26, a piezoelectric film 22 and a first electrode 24 are laminated in this order on the vibrating section 14 to form a detecting section 20. As the film forming method, there can be appropriately used a known forming method, for example, a thick film method (e.g. screen printing), a coating method (e.g. dipping) or a thin film method [e.g. ion beam, sputtering, vacuum deposition, ion plating, chemical vapor deposition (CVD) or plating]. However, the film forming method is not restricted to these methods. Among these methods, screen printing is preferred because of stable production.

A second electrode 26, leads 28 and 29 and terminal pads can be simultaneously formed by screen printing. A piezoelectric film 22 is preferably formed by screen printing, dipping or the like. In these methods, a piezoelectric film 22 can be formed on the body using a paste or a slurry each containing materials for piezoelectric film 22 and composed mainly of ceramic particles, whereby the piezoelectric film 22 can have good properties.

When a piezoelectric film 22 is formed by a film 22 forming method, since the detecting section 20 and the vibrating section can be bonded integrally without using any adhesive, this method is especially preferred because of the high reliability, reproducibility and integratability. A piezoelectric film 22 may be formed in an appropriate pattern. The pattern may be formed by screen printing, photolithography or the like, or may be formed by removing unnecessary portions using mechanical processing such as laser processing, slicing, ultrasonic processing or the like.

Each film (22, 24 and 26) thus formed on the body may be made integral with the body by heat treatment each time one film is formed, or by heat-treating these films simultaneously after formation of all films. When the first 24 and second 26 electrodes are formed by a thin film method, heat treatment is not always necessary for their integration.

Throughholes 18 may be formed in the green sheets or green tapes or in the laminating layers obtained using a mold, at the time of body formation or, by mechanical processing such as cutting, grinding, punching by pressing, or the like. That is, green sheets or the like may be machined so as to form throughholes 18 of any desired shape. Throughholes 18 may also be formed by mechanical processing such as laser processing, cutting, ultrasonic processing or the like, after sintering of the body. Throughholes 18 may also be formed after forming a detecting section, using the same processing method.

The detecting section 20 of the present particle sensor was explained above. The device utilizes the piezoelectricity of a piezoelectric film, which device detects the vibration of the vibrating section 14 and converts the vibration into electric signals by piezoelectricity of the film. However, the detecting section is not restricted to the above device utilizing piezoelectricity.

For example, the detecting section 20 may be a device utilizing electromagnetic induction. This device comprises a coil provided on the vibrating section 14 an electric circuit for detecting electric signals flowing through this coil, and a magnet (which may be an electromagnet) forming a magnetic field in the coil. When the coil vibrates together with the vibrating section 14, a current flows through the coil owing to electromagnetic induction and is detected by the electric circuit.

The detecting section 20 may be a device utilizing change in static capacity. This device comprises a pair of electrodes provided on the vibrating section 14 a dielectric held between the electrodes, and an electric circuit connected to the electrodes. The static capacity stored in this specific space is detected by the electric circuit.

The detecting section 20 may be a device utilizing change in reflected light amount. This device has a means (e.g. a photodiode) for applying a light to the vibrating section 14 and a means for measuring the amount of light reflected by the vibrating section 14. The means for measuring the amount of light reflected by the vibrating section 14 includes a photosensor. As the vibrating section 14 vibrates, the amount of light reflected by the vibrating section 14 changes, and this change in reflected light amount is measured.

The detecting section 20 may be a device utilizing change in electric resistance caused by the strain of a conductor. This device has a conductor provided on the vibrating section 14 and an electric circuit connected to this conductor. When the conductor vibrates together with the vibrating section 14, the conductor is strained by the vibration and its resistance changes, and this change in resistance is detected by the electric circuit.

The detecting section 20 may be a device utilizing change in electric resistance caused by the strain of a semiconductor.

This device has a semiconductor provided on the vibrating section 14, and an electric circuit connected to this semiconductor. When the semiconductor vibrates together with the vibrating section 14, the semiconductor is strained by the vibration and its resistance changes, and this change in resistance is detected by the electric circuit.

As appreciated from the foregoing description, in the particle sensor according to the first aspect of the present invention, the speed of a fluid colliding with the sensor element 10 can be changed so that the minimum diameter of particles detected by the sensor element 10 at each speed can be different. As a result, by changing the speed of a fluid colliding with the sensor element 10, there can be known, at each speed employed, the presence of particles of minimum detectable diameter and larger particles. By determining, in advance, the minimum detectable particle diameters at various speeds, the sizes of the particles contained in a fluid can be known quickly by simply examining the generation of signals by the sensor at various speeds. Further, by examining the number of the particles detected at each speed in a given length of time, there can be known the particle size distribution of the particles contained in the fluid.

In the particle sensor according to the second aspect of the present invention, by using, in combination, a plurality of sensors in which a fluid is allowed to collide with the respective sensor elements at different speeds and thereby the minimum particle diameters detected by the sensor elements are made different, there can be known, by each sensor, the presence of particles of minimum detectable diameter and larger particles. By determining, in advance, the minimum detectable particle diameter for each sensor, the sizes of the particles contained in a fluid can be known quickly by simply examining the generation of signals by each sensor. Further, by examining the number of the particles detected by each sensor in a given length of time, there can be known the particle size distribution of the particles contained in the fluid.

What is claimed is:

1. A particle sensor comprising:
    a sensor element comprising (a) a vibrating section having a mass that is sensitive to the collision of solid particles contained in a fluid with the vibrating section and (b) a detecting section for detecting the vibration of the vibrating section caused by said collision and converting the vibration to electric signals,
    a housing for fixing said sensor element,
    an inlet nozzle forming a fluid inlet, and
    an outlet nozzle forming a fluid outlet,
    wherein said outlet nozzle is provided so that the sensor element is between the inlet nozzle and the outlet nozzle, throughholes are formed in the sensor element in at least part of the vicinity of the vibrating section, and the fluid entering the particle sensor from the inlet nozzle collides with the sensor element, passes through the throughholes and leaves the particle sensor from the outlet nozzle, and wherein said particle sensor has such a characteristic structure that the speed of a fluid colliding with the sensor element can be changed.

2. A particle sensor according to claim 1, wherein the speed of a fluid colliding with the sensor element is changed by dividing a portion of fluid flow path located upstream of the inlet nozzle of the particle sensor into a plurality of branch flow paths, allowing each branch flow path to have a switching valve, and changing the opening state of each valve.

3. A particle sensor according to claim 1, wherein the speed of a fluid colliding with the sensor element is changed by dividing a portion of fluid flow path located downstream of the outlet nozzle of the particle sensor into a plurality of branch flow paths, allowing each branch flow path to have a switching valve, and changing the opening state of each valve.

4. A particle sensor constituted by combining a plurality of sensors each comprising:
    a sensor element comprising (a) a vibrating section having a mass that is sensitive to the collision of solid particles contained in a fluid with the vibrating section and (b) a detecting section for detecting the vibration of the vibrating section caused by said collision and converting the vibration to electric signals,
    a housing for fixing said sensor element,
    an inlet nozzle forming a fluid inlet, and
    an outlet nozzle forming a fluid outlet,
    wherein in each of said sensors said outlet nozzle is provided so that the sensor element is between the inlet nozzle and the outlet nozzle, throughholes are formed in the sensor element in at least part of the vicinity of the vibrating section, and the fluid entering the particle sensor from the inlet nozzle collides with the sensor element, passes through the throughholes and leaves the particle sensor from the outlet nozzle, and wherein said particle sensor has such a characteristic structure that a fluid is allowed to collide with the sensor elements of the individual sensors at different speeds.

5. A particle sensor according to claim 4, wherein the collision of a fluid with the sensor elements of the individual sensors at different speeds is achieved by allowing the inlet nozzles of the individual sensors to have different inner diameters.

6. A particle sensor according to claim 4, wherein the collision of a fluid with the sensor elements of the individual sensors at different speeds is achieved by allowing the distances between inlet nozzle top end and sensor element of the individual sensors to have different values.

7. A particle sensor according to claim 4, wherein the collision of a fluid with the sensor elements of the individual sensors at different speeds is achieved by allowing a fluid to have different flow resistances downstream of the individual sensors.

8. A particle sensor according to claim 4, wherein the collision of a fluid with the sensor elements of the individual sensors at different speeds is achieved by allowing a fluid to have different flow resistances upstream of the sensor elements of the individual sensors.

9. A particle sensor according to claim 4, wherein the collision of a fluid with the sensor elements of the individual sensors at different speeds is achieved by allowing a fluid to be fed into the sensor elements of the individual sensors at different amounts per unit time.

* * * * *